(12) United States Patent
Hong et al.

(10) Patent No.: US 12,033,299 B2
(45) Date of Patent: Jul. 9, 2024

(54) INTERACTION TRAINING SYSTEM FOR AUTISTIC PATIENT USING IMAGE WARPING, METHOD FOR TRAINING IMAGE WARPING MODEL, AND COMPUTER READABLE STORAGE MEDIUM INCLUDING EXECUTIONS CAUSING PROCESSOR TO PERFORM SAME

(71) Applicant: Seoul National University Hospital, Seoul (KR)

(72) Inventors: Soonbum Hong, Seoul (KR); Hyoun-Joong Kong, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 56 days.

(21) Appl. No.: 17/951,944

(22) Filed: Sep. 23, 2022

(65) Prior Publication Data

US 2023/0123330 A1    Apr. 20, 2023

(30) Foreign Application Priority Data

Jul. 26, 2021    (KR) .................... 10-2021-0097811

(51) Int. Cl.
*G06T 3/00*    (2024.01)
*G06F 3/01*    (2006.01)
(Continued)

(52) U.S. Cl.
CPC ............... *G06T 3/18* (2024.01); *G06F 3/011* (2013.01); *G06V 10/40* (2022.01); *G06V 10/761* (2022.01);
(Continued)

(58) Field of Classification Search
CPC .......... G06T 3/18; G16H 50/30; G16H 30/40; G06V 10/761; G06V 10/40; G06V 10/774; G06F 3/011; A61B 5/165
See application file for complete search history.

(56) References Cited

U.S. PATENT DOCUMENTS

2019/0029528 A1*  1/2019  Tzvieli ................. A61B 5/6814
2020/0175655 A1*  6/2020  Grossinger ........... G06T 15/205
(Continued)

FOREIGN PATENT DOCUMENTS

KR      20210012789 A  *  1/2021  ............ G16H 20/70
KR      10-2216899 B1      2/2021
(Continued)

OTHER PUBLICATIONS

Donggyue Chen et al., "Face Swapping: Realistic Image Synthesis Based on Facial Landmarks Alignment", Hindawi, vol. 2019, No. 8902701, pp. 1-11, Mar. 14, 2019.
(Continued)

*Primary Examiner* — Terrell M Robinson
(74) *Attorney, Agent, or Firm* — Bridgeway IP Law Group, PLLC; Jihun Kim

(57) ABSTRACT

There is provided a user interaction training system. The user interaction training system comprises: a photographing device configure to photograph an original image including a first object at a plurality of photographing angles; an image warping device configured to receive an image including a second object corresponding to a user and the original image including the first object photographed by the photographing device, and to generate a converted image converting the first object into a third object different from the first object based on characteristic information of the second object by using a pre-trained image warping model; and a display device configured to display the generated converted image.

12 Claims, 6 Drawing Sheets

(51) Int. Cl.
  *G06T 3/18* (2024.01)
  *G06V 10/40* (2022.01)
  *G06V 10/74* (2022.01)
  *G06V 10/774* (2022.01)
  *G16H 30/40* (2018.01)
  *G16H 50/30* (2018.01)
  *A61B 5/16* (2006.01)

(52) U.S. Cl.
  CPC ........... *G06V 10/774* (2022.01); *G16H 30/40* (2018.01); *G16H 50/30* (2018.01); *A61B 5/165* (2013.01)

(56) References Cited

U.S. PATENT DOCUMENTS

2021/0022657 A1* 1/2021 Voss .................... G06V 10/255
2021/0295025 A1* 9/2021 Sud ........................ G06F 1/163

FOREIGN PATENT DOCUMENTS

| KR | 102216899 B1 * | 2/2021 | ............. G16H 20/70 |
| KR | 10-2021-0028786 A | 3/2021 | |
| KR | 20210028786 A * | 3/2021 | ............. G16H 20/70 |
| KR | 10-2277820 B1 | 7/2021 | |

OTHER PUBLICATIONS

Mi Mi Kim, "Office Action for Korean Application No. 10-2021-0097811", Aug. 16, 2023, KIPO, Republic of Korea.

* cited by examiner

INTERACTION TRAINING SYSTEM FOR AUTISTIC PATIENT USING IMAGE WARPING, METHOD FOR TRAINING IMAGE WARPING MODEL, AND COMPUTER READABLE STORAGE MEDIUM INCLUDING EXECUTIONS CAUSING PROCESSOR TO PERFORM SAME

TECHNICAL FIELD

The present disclosure relates to an interactive training system for an autistic patient using a warping technique and a method for training an image warping model.

BACKGROUND

Recently, with the development of cognitive science and technology, interest in devices for enhancing social skills for pre-school or later children with autism spectrum disorder is increasing.

However, in order to improve the social skills of the current target child, it is necessary to first make the child feel psychologically stable with respect to others. In addition, it is necessary to develop skills that allow children to gradually interact with others according to their familiarity.

SUMMARY

A problem to be solved according to an embodiment of the present disclosure includes converting an image of another person into another object according to familiarity with the child and providing the converted image.

Other objects not specified in this specification may be additionally considered within a range that can be easily inferred from the following detailed description and effects thereof.

In accordance with an aspect of the present disclosure, there is provided a user interaction training system. The user interaction training system may comprise: a photographing device configure to photograph an original image including a first object at a plurality of photographing angles; an image warping device configured to receive an image including a second object corresponding to a user and the original image including the first object photographed by the photographing device, and to generate a converted image converting the first object into a third object different from the first object based on characteristic information of the second object by using a pre-trained image warping model; and a display device configured to display the generated converted image.

The first object may be an object in which a frequency of interaction with the user is less than or equal to a predetermined first reference, and the second object is an object in which the frequency of interaction with the user exceeds a predetermined second reference.

The converted image converted into the third object may be converted to have a closer similarity to the second object than the first object.

The display device may comprise a head-mounted display worn by the user.

The photographing device may be configured to photograph a scene within a field of view of a user wearing the display device.

The image warping model may be trained to receive a training image including an arbitrary object, and to reconstruct and output the training image based on a feature value extracted from the second object.

The user interaction training system further comprise a sensor configured to measure a stress index of the user, wherein the sensor is configured to measure the stress index of the user with respect to the converted image generated while the user wears the display device.

The image warping model may be trained to reconstruct the training image further based on the stress index.

The image warping apparatus reconstructs the converted image by further reflecting the stress index in the image warping model, and if the stress index is less than or equal to a preset first reference stress value, the image warping apparatus reconstructs the converted image such that a first similarity between the third object and the first object becomes greater than a second similarity between the third object and the second object.

The image warping apparatus reconstructs the converted image by further reflecting the stress index in the image warping model, and if the stress index exceeds a preset second reference stress value, the image warping apparatus reconstructs the converted image such that a second similarity between the third object and the second object becomes greater than a first similarity between the third object and the first object.

In accordance with another aspect of the present disclosure, there is provided a method for training an image warping model performed by an image warping model training apparatus. The method for training an image warping model may comprise: receiving an input of a training image including an arbitrary object; and adjusting a parameter of at least one layer of the image warping model so that the image warping model outputs a converted image obtained by reconstructing the training image based on a feature value extracted from a conversion reference target. The conversion reference target may be a target whose interaction frequency with the user exceeds a preset reference.

The method for training an image warping model may comprise receiving a stress index of the user for the converted image; and updating the parameter based on the stress index.

The updating of the parameter may comprise identifying a first similarity of the converted image with the arbitrary object and a second similarity of the converted image with the conversion reference object; and updating the parameter based on the stress index, the first similarity, and the second similarity.

The updating of the parameter may comprise updating the parameter so that the first similarity becomes greater than the second similarity if the stress index for the converted image is less than or equal to a preset first reference stress value.

The updating of the parameter may comprise updating the adjusted parameter so that the second similarity becomes greater than the first similarity if the stress index for the converted image exceeds a preset second reference stress value.

In accordance with another aspect of the present disclosure, there is provided a non-transitory computer-readable storage medium storing a computer program, comprising commands for a processor to perform a method for training image warping model. The method for training image warping model may comprise: receiving an input of a training image including an arbitrary object; and adjusting a parameter of at least one layer of the image warping model so that the image warping model outputs a converted image obtained by reconstructing the training image based on a feature value extracted from a conversion reference target.

The conversion reference target is a target whose interaction frequency with the user exceeds a preset reference.

The method for training image warping model may comprise receiving a stress index of the user for the converted image; and updating the parameter based on the stress index.

The updating of the parameter may comprise identifying a first similarity of the converted image with the arbitrary object and a second similarity of the converted image with the conversion reference object; and updating the parameter based on the stress index, the first similarity, and the second similarity.

The updating of the parameter may comprise updating the parameter so that the first similarity becomes greater than the second similarity if the stress index for the converted image is less than or equal to a preset first reference stress value.

The updating of the parameter may comprise updating the parameter so that the second similarity becomes greater than the first similarity if the stress index for the converted image exceeds a preset second reference stress value.

In accordance with another aspect of the present disclosure, there is provided a computer program in stored a non-transitory computer-readable storage medium including computer executable instructions, wherein the instructions, when executed by a processor, cause the processor to perform a method for training image warping model. The method for training image warping model may comprise: receiving an input of a training image including an arbitrary object; and adjusting a parameter of at least one layer of the image warping model so that the image warping model outputs a converted image obtained by reconstructing the training image based on a feature value extracted from a conversion reference target. The conversion reference target is a target whose interaction frequency with the user exceeds a preset reference.

As described above, according to the embodiments of the present disclosure, an image of another person may be converted into another object according to familiarity with a child using a pre-trained image warping model, and may be provided through glasses or head mounted display (HMD) devices.

By using smart glasses or HMD devices to convert images of others into different objects according to their familiarity with the child, children can feel psychological stability and take a favorable attitude toward interpersonal relationships by reducing stress.

Even if effects not explicitly mentioned herein, the effects described in the following specification expected by the technical features of the present disclosure and their potential effects are treated as described in the specification of the present disclosure.

DETAILED DESCRIPTION

Figure 1:
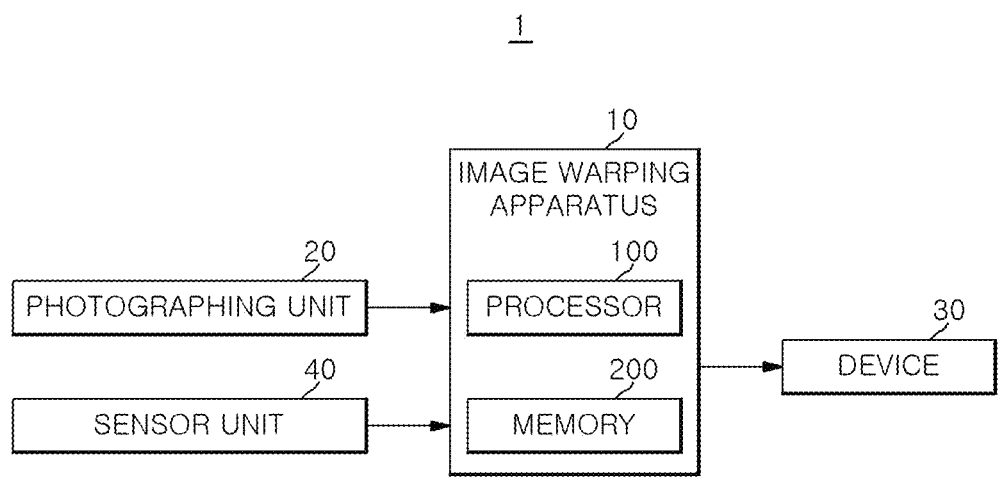
FIG. 1 is a block diagram illustrating an interactive training system for an autistic patient using a warping technique according to an embodiment of the present disclosure.

Hereinafter, an interactive training system and an image warping model training method for an autistic patient using a warping technique related to the present disclosure will be described in more detail with reference to the drawings. However, the present disclosure may be embodied in several different forms, and may not be limited to the described embodiments. In addition, in order to clearly explain the present disclosure, parts irrelevant to the description are omitted, and the same reference numerals in the drawings indicate the same members.

The suffixes "module" and "part" for the components used in the following description are given or mixed in consideration of only the ease of writing the specification, and do not have distinct meanings or roles by themselves.

An embodiment of the present disclosure relates to an interactive training system for an autistic patient using a warping technique and a method for training an image warping model.

FIG. 1 is a block diagram illustrating an interactive training system for an autistic patient using a warping technique according to an embodiment of the present disclosure.

Referring to FIG. 1, the interactive training system 1 for the autistic patient using the warping technique according to the embodiment of the present disclosure includes an image warping device 10, a photographing unit 20, a device 30, and a sensor unit 40.

The interaction training system 1 for the autistic patient using the warping technique according to the embodiment of the present disclosure is an interactive training system to provide psychological stability and relieve pain to users with neurodevelopmental disorders and autism spectrum disorders by making a person that the wearer is staring look like a familiar object to the wearer, by using a computer vision-based AI algorithm.

According to various embodiments of the present disclosure, the familiar object may include not only a person familiar with the wearer, but also various objects such as a companion animal of the wearer, a friendly animal, and a character of an animation image familiar to the wearer.

The photographing unit 20 photographs an original image including the first object at a plurality of photographing angles. The photographing unit 20 may be an imaging device including a camera capable of acquiring an image or a moving picture.

The photographing unit 20 may photograph the face and the expression of an unfamiliar object from angles such as the front, left, and right sides of the first object as the original image including the first object is photographed from a plurality of photographing angles.

The photographing unit 20 photographs a scene within the field of view of a user wearing the device, and may be implemented integrally with the device 30, or may be separately provided on the user's body or outside the user's body.

The image warping apparatus 10 includes a processor 100 and a memory 200.

The memory 200 may store an image including a pre-trained image warping model and a plurality of objects.

The processor 100 of the image warping device 10 receives an image including a second object corresponding to the user and an original image including a first object photographed by the photographing unit, and generates a converted image obtained by converting the first object into a third object different from the first object based on the characteristic information of the second object by using a pre-trained image warping model.

Here, the first object may be an object whose interaction frequency with the user is equal to or less than a predetermined first reference, and the second object may be an object whose interaction frequency with the user exceeds the predetermined second reference.

The frequency of interaction with the user indicates familiarity with the user, and the frequency is high in case spending a lot of time with them such as family, friends, and a nanny. If the number of meetings is small, such as a childcare teacher, a nurse, a stranger, or someone you meet at the first place, the frequency is low.

Also, according to various embodiments of the present disclosure, the first object may include not only an unfamiliar person, but also an unfamiliar virtual person, a virtual avatar, and the like, and the second object may include not only the person but also various objects such as the wearer's companion, familiar animals, and characters of animation images familiar to the wearer.

Also, the converted image converted into the third object may be an image obtained by synthesizing a face similarly to a familiar object, and may be converted to have a closer similarity to the second object than the first object.

For example, in the case of an image converted to a third object using an image of a first object that is a stranger and a second object corresponding to the mother, the image is converted to be more similar to the second object, and the similarity can be changed gradually depending on the degree of the user's interaction.

Here, the similarity means that the feature values of the pixels of the image for each object have a high degree of agreement with each other. That is, the second object may be a conversion reference target.

If the first object is encountered for the first time, an image converted into a third object is generated to be similar to the second object side. However, if the frequency of interaction with the first object gradually increases, and if it is analyzed to be familiar with the first object as a result of measuring the user's stress index, it is possible to generate an image converted into a third object by changing the degree of similarity to be more similar to the first object than the first time.

Also, the processor 100 may continuously train the image warping model.

The image warping model is trained to receive a training image including an arbitrary target, and to reconstruct and output the training image based on the feature values extracted from the conversion reference target.

Here, the conversion reference target refers to a target whose interaction frequency with the user exceeds a preset reference, and is preferably a user-friendly target.

The device 30 displays the generated converted image.

Here, the device includes a head-mounted display worn by the user.

The head-mounted display is used as a display device for realization of virtual reality or augmented reality, and may be grafted with 3D display technology.

The sensor unit 40 measures the user's stress index, and specifically measures the user's stress index for the converted image generated while the user wears the device.

The sensor unit 40 may detect eye tracking information (video nystagmography (VNG), electrical oculography (EOG)), HRV, GSR, voice signals, etc., and may collect signals by including an eye tracking camera sensor and EOG electrode in the HMD.

Since HRV (heart rate variability) and GSR (galvanic skin response) vary depending on the user's stress and tension, HRV and GSR changes are monitored while checking the converted image.

Here, the stress index is indicated by measuring the physical and mental responses that appear to the user after the user identifies the third object through the device.

Thereafter, the image warping model may be trained to reconstruct the training image further based on the stress index.

The sensor unit 40 may be attached to the user's body, and may detect factors such as anxiety using an internal monitoring function of the device.

Figure 2:
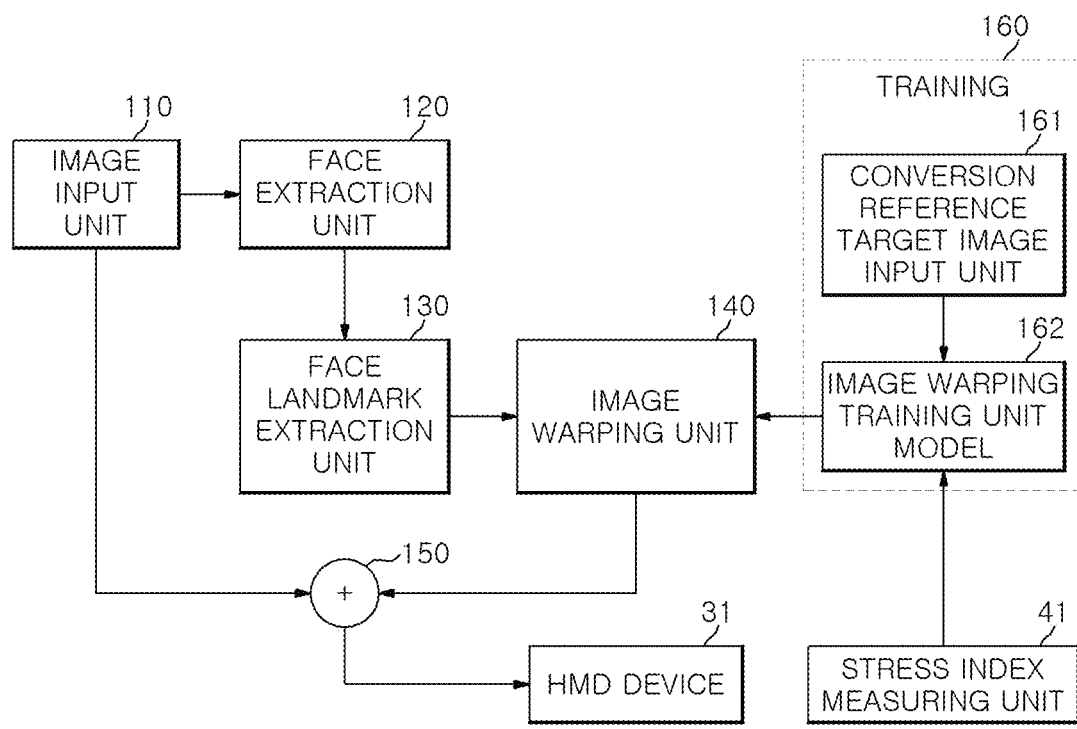
FIG. 2 is a block diagram illustrating an image warping apparatus of the interactive training system for the autistic patient using the warping technique according to the embodiment of the present disclosure.

FIG. 2 is a block diagram illustrating the image warping apparatus of the interactive training system for the autistic patient using the warping technique according to the embodiment of the present disclosure.

Referring to FIG. 2, the image warping apparatus 10 of the interactive training system for the autistic patient using the warping technique according to the embodiment of the present disclosure may include an image input unit 110, a face extraction unit 120, and a face landmark extraction unit 130, an image warping unit 140 and an image synthesizing unit 150, and may also include a conversion reference target image input unit 161 and an image warping model training unit 162 of a processor 160 for training the neural network.

The image input unit 110 receives an original image including the first object captured by the photographing unit, and the face extraction unit 120 extracts a region corresponding to the face of the first object from the original image. Thereafter, the face landmark extraction unit 130 extracts a landmark of the face including the eyes, nose, mouth, jaw line, eyebrows, and the like.

In this case, a layout may be generated in the part where the face is recognized, and a plurality of points such as eyes, nose, mouth, chin line, and eyebrow, and connection lines connecting the points may be generated.

Thereafter, landmark coordinates and recognized face coordinates may be acquired, and a feature value may be extracted for each pixel of the original image based on this.

The image warping unit 140 performs image warping so that the first object of the original image is similar to the second object. Image warping is a technique of geometric processing that moves the position of a pixel.

Geometric processing such as enlargement or reduction of an image obtains a uniform return result by applying a certain rule to all pixels. On the other hand, in image warping, the degree of movement may be different for each pixel.

The image warping unit 140 determines and converts a movement degree for each pixel so as to be similar to the second object by using the image warping model trained with respect to the pixel-specific feature values extracted from the first object of the original image.

Here, the conversion reference target image input unit 161 receives a training image including an arbitrary target, and the image warping model training unit 162 reconstructs and outputs the training image based on the feature values extracted from the conversion reference target, thereby the degree of movement for each pixel is determined.

Thereafter, if an image including the first object is input, the image warping unit 140 converts the image of the first object to be similar to the second object, i.e., the conversion reference target according to the degree of movement for each pixel. The image synthesizing unit 150 generates a composite face similar to the second object.

The generated converted image is provided to a user through a display of the device, and the device may include the HMD device 31. The user measures the user's stress index for the converted image through the stress index measuring unit 41 while checking the converted image.

Here, the stress index is indicated by measuring the physical and mental responses that appear to the user after the user identifies the third object through the device.

Thereafter, the image warping model may be trained to reconstruct the training image further based on the stress index.

Figure 3:
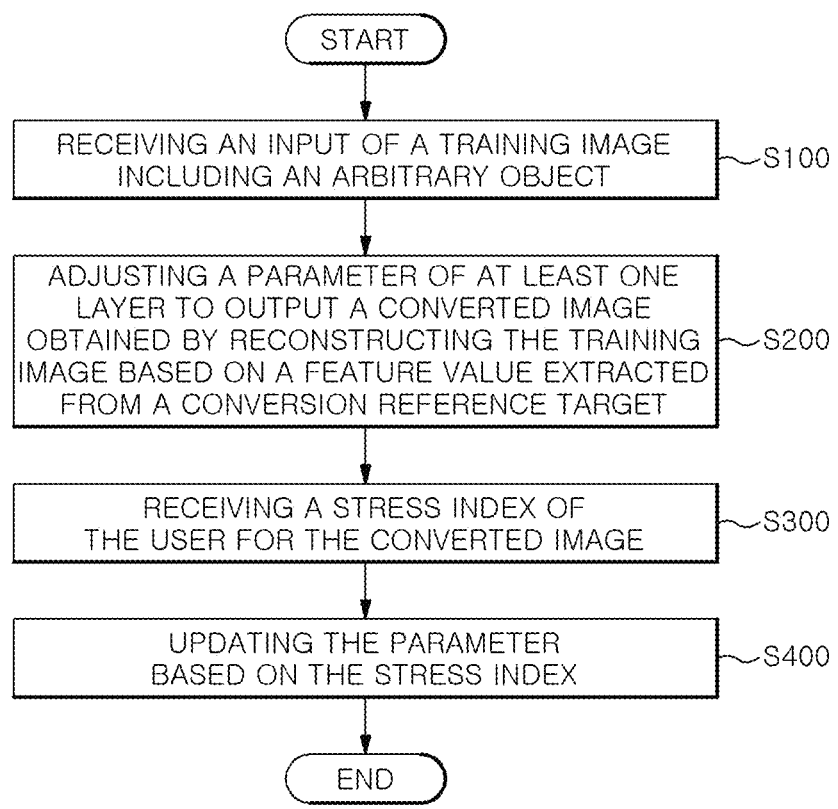
FIG. 3 is a flowchart illustrating a method for training an image warping model according to the embodiment of the present disclosure.

FIG. 3 is a flowchart illustrating a method for training the image warping model according to the embodiment of the present disclosure.

Referring to FIG. 3, the image warping model training method according to the embodiment of the present disclosure is performed by an image warping model training apparatus. In step S100, a training image including an arbitrary object is received.

In step 200, based on the feature values extracted from the conversion reference target, parameters of at least one layer are adjusted to output a converted image reconstructed from the training image.

Here, the conversion reference target is a target whose interaction frequency with the user exceeds a preset reference.

In step S300, the user's stress index for the converted image is input.

In step S400, the parameter is updated further based on the stress index.

Figure 4:
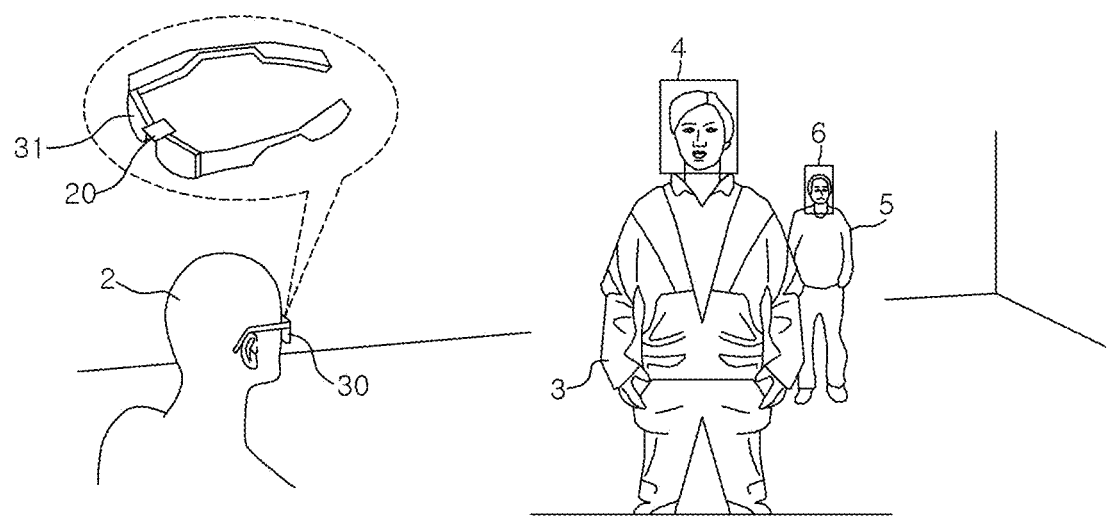
FIG. 4 is an example of an environment for recognizing a first object using the interactive training system for the autistic patient using the warping technique according to the embodiment of the present disclosure.

FIG. 4 is an example of an environment for recognizing the first object using the interactive training system for the autistic patient using the warping technique according to the embodiment of the present disclosure.

Referring to FIG. 4, a user may wear the device 30, and the device 30 may include a photographing unit 20.

The device according to some embodiments may be an AR glass device, and the AR glass device may be worn on the head of the user 2 in the same manner as glasses.

While FIG. 4 shows the user wearing AR glasses, according to various embodiments of the present disclosure, the user may use is a device providing a virtual reality (VR) service, a device providing an augmented reality (AR) service, and a device providing mixed reality (MR) service. The AR glass device may transmit visual information to the user 2 wearing the AR glass device 30 through the display 31. The AR glass device 30 may display, for example, a user interface for controlling the AR glass device 30, a user interface for displaying the status of the AR glass device 30, and the like, through the display 31.

The display 31 of the AR glass device 30 may use, for example, at least one method among a semi-reflective curved mirror type capable of optical see-through, a light guide type, or a waveguide type. The AR glass device 30 may provide the user 2 with an augmented reality experience by transmitting information about a three-dimensional image through the display 31 capable of optically seeing through.

Here, the photographing unit 20 photographs a scene within the field of view of the user 2 wearing the device 30, and if the user sees the objects 3, 5 facing through the device, the photographing unit 20 transmits an image including the objects 3 and 5 as an original image to the image warping device.

The photographing unit 20 according to some embodiments may be a camera, and the AR glass device 30 may capture a preview image including at least one object located in front of the AR glass device 30 through the camera. In FIG. 4, the camera 20 of the AR glass device 30 is illustrated as being located in the front center of the AR glass device 20, but the location of the camera 20 is not necessarily limited thereto.

The image warping apparatus recognizes the faces 4, 6 of the objects 3, 5 respectively, and converts them into a familiar object to be converted, and then provides the converted image to the user through the display 31 of the device 30.

Accordingly, after the user 2 wears the device 30, the faces 4, 6 of the objects 3, 5 may be recognized as faces similar to those of the familiar objects.

In another embodiment, when using a device providing a virtual reality (VR) service, the user 2 may be provided with a converted image converted into a familiar object in a virtual environment.

In the case of using the virtual reality (VR) service, since the virtual environment can be changed to a space familiar to the user and provided, the user can interact with the object more stably.

When looking at another person's face while wearing these glasses, it is possible to change the other person's face to resemble a familiar person so that the wearer can feel psychological stability and take a favorable attitude toward interpersonal relationships by reducing stress.

In addition, it is possible to reduce the psychological burden by having people who deal with a large number of people, such as public lectures or interviews, wear these glasses, so it can be applied not only to autistic patients but also to people who want to train interaction.

Figure 5:
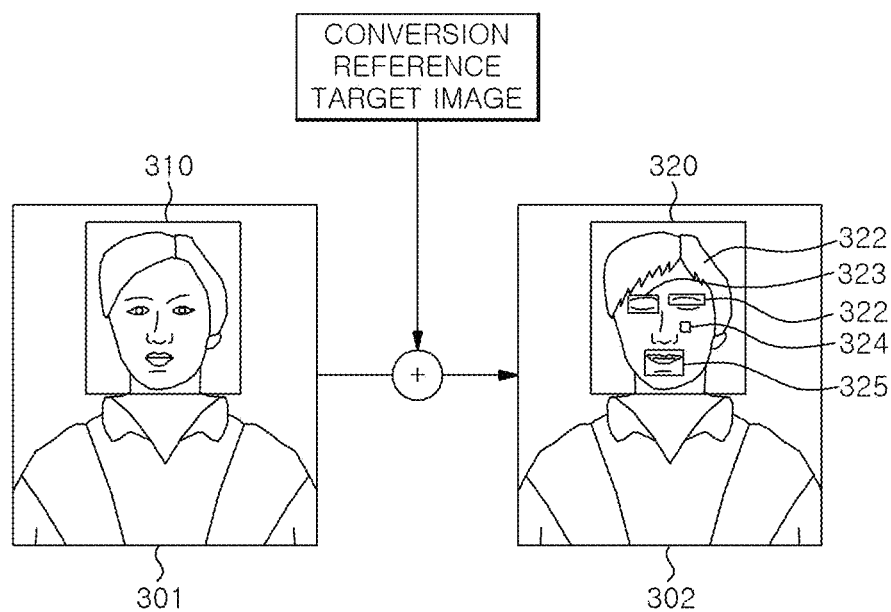
FIG. 5 is an example of a converted image generated using the image warping model in the interactive training system for the autistic patient using the warping technique according to the embodiment of the present disclosure.

FIG. 5 is an example of a converted image generated using the image warping model in the interactive training system for the autistic patient using the warping technique according to the embodiment of the present disclosure.

A partial image 301 of FIG. 5 is a separate extraction of the face 4 of the unfamiliar object 3 in FIG. 4. Specifically, the region 310 corresponding to the face of the first object is extracted from the original image, and landmarks of the face including eyes, nose, mouth, jaw line, and eyebrows are extracted.

Here, landmark coordinates and recognized face coordinates may be acquired, and feature values may be extracted for each pixel of the original image based on them.

Thereafter, an image of a familiar target, which is a second object, may be input, and a movement degree for each pixel of the original image may be determined so that the first object becomes similar to the second object by using the image warping model. Then, image conversion may be performed by reflecting the pixel-specific feature value extracted from the first object of the original image at a position corresponding to the determined movement degree for each pixel.

According to various embodiments of the present disclosure, the familiar target, which is the second object, may include not only a person familiar with the wearer, but also various targets such as a companion animal of the wearer, a friendly animal, and a character of an animation image familiar to the wearer.

In the case of animals and characters, after applying the appearance of the second object as an animated character or a cat at the time of applying the warping technology, parameters of the image warping model may be adjusted.

According to the embodiment of the present disclosure, the image warping model includes a generative adversarial network (GAN) and may be implemented including a generator and a discriminator.

Accordingly, by converting the image of the first object according to the degree of movement for each pixel to be converted to be similar to the second object, a converted image 302 of the third object as shown in FIG. 5 may be obtained.

As shown in FIG. 5, according to the region 320 corresponding to the face of the second object in the converted image 302, the head 321, the eyebrow 322, the shape of the eye and the expression of the eye 323, the point or the wrinkle of the cheek 324, the shape according to the shape and expression of the lips 325 may be converted.

Figure 6A:
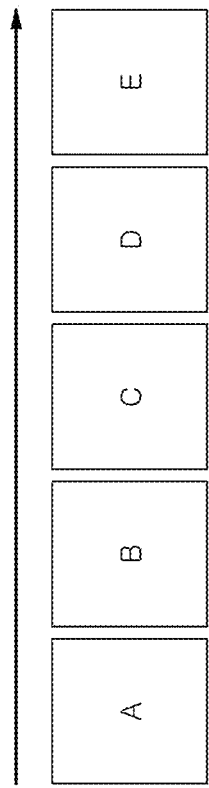
FIGS. 6A and 6B are diagrams illustrating training of the image warping model according to a stress index in the interactive training system for the autistic patient using the warping technique according to the embodiment of the present disclosure.
Figure 6B:
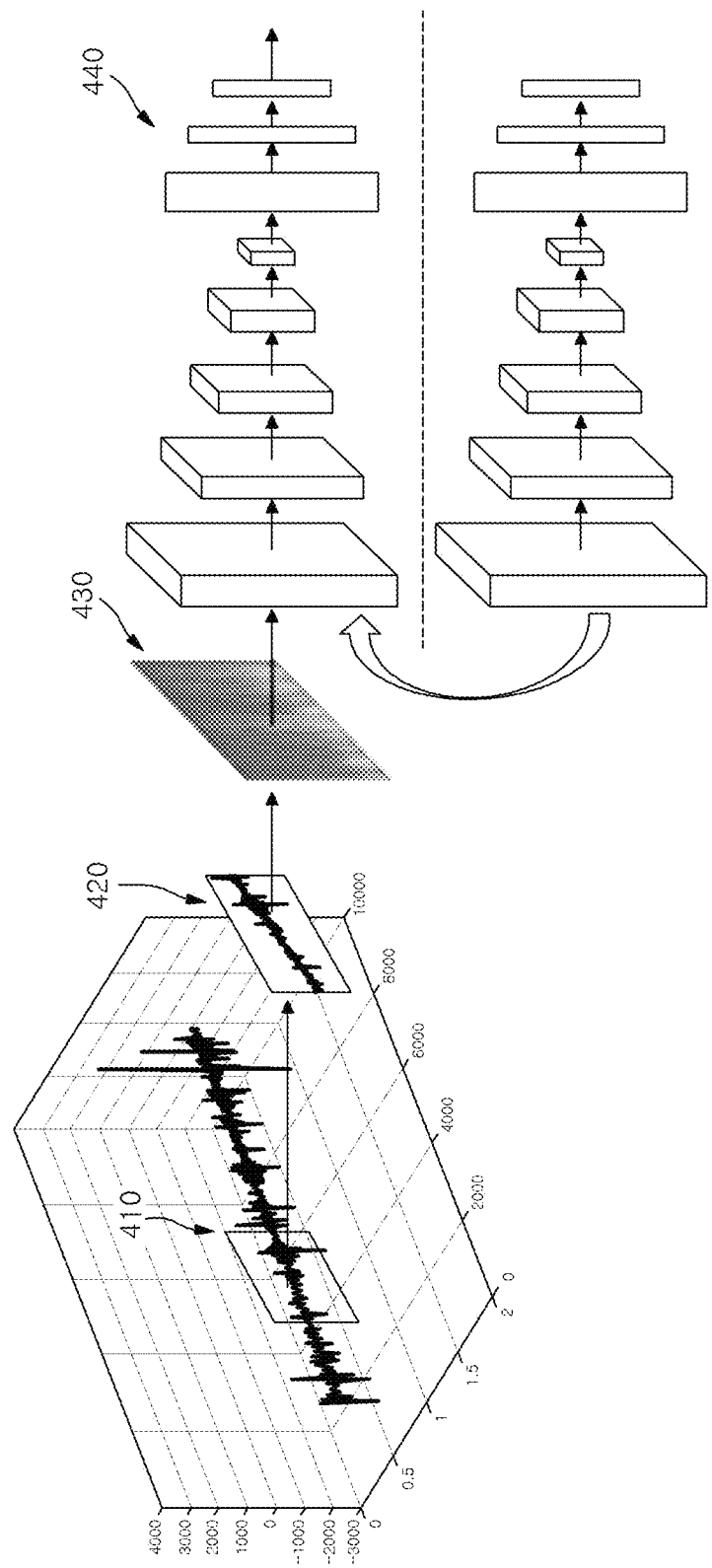

FIGS. 6A and 6B are diagrams illustrating training of the image warping model according to a stress index in the interactive training system for the autistic patient using the warping technique according to the embodiment of the present disclosure.

As shown in FIG. 6A, according to the embodiment of the present disclosure, the degree of change to the face of the second object can be adjusted while maintaining the facial expression of the first object.

For example, an image corresponding to a first object that is a stranger is an image A, an image corresponding to a second object that is a familiar person is an image E, and the converted image may be converted to be more similar to the second object in the order of B, C, and D images.

If the first object is encountered for the first time, an image converted into a third object is generated to be similar to the second object side. However, if the frequency of interaction with the first object gradually increases, and it is analyzed as familiar with the first object as a result of measuring the user's stress index, an image converted into a third object may be generated by changing the degree of similarity to be more similar to the first object than the first time.

To this end, as shown in FIG. 6B, the image warping model may be trained to reconstruct the training image further based on the stress index.

In order to train the image warping model, the user's EMG signal is received through the input unit 410, and the EMG signal at the time point when the conversion reference target is identified from the user's EMG signal through the sample extraction unit 420 is extracted. Thereafter, the EMG signal is converted into a spectral diagram indicating emitted light or sound region as the main feature center in the spectrogram conversion unit 430, and the parameters of the image warping model 440 is updated using the converted spectrum diagram.

The input unit 410 may receive, through the sensor unit 40, in addition to the user's EMG signal, eye tracking information (VNG, EOG), HRV, GSR, voice signal, and the like.

Here, the stress index is indicated by measuring the physical and mental responses that appear to the user after the user identifies the third object through the device.

Thereafter, the image warping model may be trained to reconstruct the training image further based on the stress index.

If the user's stress index is high, the parameters of the image warping model may be updated to be similar to the characteristic values of the pixels of the familiar target image. If the user's stress index is low, the parameter of the image warping model may be updated to be similar to the feature value of the pixel of the unfamiliar target image.

Also, updating the parameters of the image warping model according to the user's stress index may be automatically implemented by the processor.

In addition, as a computer-readable recording medium storing a computer program, there may be provided a computer-readable recording medium storing a computer program including commands for causing the processor to perform the image warping model training method.

In addition, as a computer program stored in a computer-readable recording medium, there may be provided a computer program including commands for causing the processor to perform the image warping model training method.

Combinations of steps in each flowchart attached to the present disclosure may be executed by computer program instructions. Since the computer program instructions can be mounted on a processor of a general-purpose computer, a special purpose computer, or other programmable data processing equipment, the instructions executed by the processor of the computer or other programmable data processing equipment create a means for performing the functions described in each step of the flowchart. The computer program instructions can also be stored on a computer-usable or computer-readable storage medium which can be directed to a computer or other programmable data processing equipment to implement a function in a specific manner. Accordingly, the instructions stored on the computer-usable or computer-readable recording medium can also produce an article of manufacture containing an instruction means which performs the functions described in each step of the flowchart. The computer program instructions can also be mounted on a computer or other programmable data processing equipment. Accordingly, a series of operational steps are performed on a computer or other programmable data processing equipment to create a computer-executable process, and it is also possible for instructions to perform a computer or other programmable data processing equipment to provide steps for performing the functions described in each step of the flowchart.

In addition, each step may represent a module, a segment, or a portion of codes which contains one or more executable instructions for executing the specified logical function(s). It should also be noted that in some alternative embodiments, the functions mentioned in the steps may occur out of order. For example, two steps illustrated in succession may in fact be performed substantially simultaneously, or the steps may sometimes be performed in a reverse order depending on the corresponding function.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. A user interaction training system, comprising:
a photographing device configure to photograph an original image including a first object at a plurality of photographing angles;
an image warping device configured to receive an image including a second object corresponding to a user and the original image including the first object photographed by the photographing device, and to generate a converted image converting the first object into a third object different from the first object based on characteristic information of the second object by using a pre-trained image warping model;
a display device configured to display the generated converted image; and
a sensor configured to measure a stress index of the user,
wherein the image warping model is trained to receive a training image including an arbitrary object, to reconstruct and output the training image based on a feature value extracted from the second object and the stress index,
wherein the sensor is configured to measure the stress index of the user with respect to the converted image generated while the user wears the display device, and
wherein the image warping device reconstructs the converted image by further reflecting the stress index in the image warping model, and if the stress index is less than or equal to a preset first reference stress value, the image warping device reconstructs the converted image such that a first similarity between the third object and the first object becomes greater than a second similarity between the third object and the second object.

2. The system of claim 1, wherein the first object is an object in which a frequency of interaction with the user is less than or equal to a predetermined first reference, and the second object is an object in which the frequency of interaction with the user exceeds a predetermined second reference.

3. The system of claim 1, wherein the converted image converted into the third object is converted to have a closer similarity to the second object than the first object.

4. The system of claim 1, wherein the display device comprises a head-mounted display worn by the user.

5. The system of claim 1, wherein the photographing device is configured to photograph a scene within a field of view of a user wearing the display device.

6. A user interaction training system, comprising:
a photographing device configure to photograph an original image including a first object at a plurality of photographing angles;
an image warping device configured to receive an image including a second object corresponding to a user and the original image including the first object photographed by the photographing device, and to generate a converted image converting the first object into a third object different from the first object based on characteristic information of the second object by using a pre-trained image warping model;
a display device configured to display the generated converted image; and
a sensor configured to measure a stress index of the user,
wherein the image warping model is trained to receive a training image including an arbitrary object, to reconstruct and output the training image based on a feature value extracted from the second object and the stress index,
wherein the sensor is configured to measure the stress index of the user with respect to the converted image generated while the user wears the display device, and
wherein the image warping device reconstructs the converted image by further reflecting the stress index in the image warping model, and if the stress index exceeds a preset second reference stress value, the image warping device reconstructs the converted image such that a second similarity between the third object and the second object becomes greater than a first similarity between the third object and the first object.

7. A method for training an image warping model performed by an image warping model training apparatus,
receiving an input of a training image including an arbitrary object; and
adjusting a parameter of at least one layer of the image warping model so that the image warping model outputs a converted image obtained by reconstructing the training image based on a feature value extracted from a conversion reference target to a user,
wherein the conversion reference target is a target whose interaction frequency with the user exceeds a preset reference,
wherein the adjusting the parameter further comprises:
identifying a first similarity of the converted image with the arbitrary object and a second similarity of the converted image with the conversion reference object;
updating the parameter based on a stress index, the first similarity, and the second similarity; and
updating the parameter so that the first similarity becomes greater than the second similarity if the stress index for the converted image is less than or equal to a preset first reference stress value.

8. The method of claim 7, further comprising:
receiving a stress index of the user for the converted image; and
updating the parameter based on the stress index.

9. A method for training an image warping model performed by an image warping model training apparatus,
receiving an input of a training image including an arbitrary object; and
adjusting a parameter of at least one layer of the image warping model so that the image warping model outputs a converted image obtained by reconstructing the training image based on a feature value extracted from a conversion reference target to a user,
wherein the conversion reference target is a target whose interaction frequency with the user exceeds a preset reference,
wherein the adjusting the parameter further comprises:
identifying a first similarity of the converted image with the arbitrary object and a second similarity of the converted image with the conversion reference object;
updating the parameter based on a stress index, the first similarity, and the second similarity; and
updating the adjusted parameter so that the second similarity becomes greater than the first similarity if the stress index for the converted image exceeds a preset second reference stress value.

10. A non-transitory computer-readable storage medium including computer executable instructions, wherein the instructions, when executed by a processor, cause the processor to perform a method for training an image warping model, the method comprising:
    receiving an input of a training image including an arbitrary object; and
    adjusting a parameter of at least one layer of the image warping model so that the image warping model outputs a converted image obtained by reconstructing the training image based on a feature value extracted from a conversion reference target to a user,
    wherein the conversion reference target is a target whose interaction frequency with the user exceeds a preset reference,
    wherein the adjusting the parameter further comprises:
        identifying a first similarity of the converted image with the arbitrary object and a second similarity of the converted image with the conversion reference object;
        updating the parameter based on a stress index, the first similarity, and the second similarity; and
        updating the parameter so that the first similarity becomes greater than the second similarity if the stress index for the converted image is less than or equal to a preset first reference stress value.

11. The non-transitory computer-readable storage medium of claim 10, wherein the method further comprises:
    receiving a stress index of the user for the converted image; and
    updating the parameter based on the stress index.

12. A non-transitory computer-readable storage medium including computer executable instructions, wherein the instructions, when executed by a processor, cause the processor to perform a method for training an image warping model, the method comprising:
    receiving an input of a training image including an arbitrary object; and
    adjusting a parameter of at least one layer of the image warping model so that the image warping model outputs a converted image obtained by reconstructing the training image based on a feature value extracted from a conversion reference target to a user,
    wherein the conversion reference target is a target whose interaction frequency with the user exceeds a preset reference,
    wherein the adjusting the parameter further comprises:
        identifying a first similarity of the converted image with the arbitrary object and a second similarity of the converted image with the conversion reference object;
        updating the parameter based on a stress index, the first similarity, and the second similarity; and
        updating the parameter so that the second similarity becomes greater than the first similarity if the stress index for the converted image exceeds a preset second reference stress value.

* * * * *